United States Patent [19]
Rosenblatt

[11] Patent Number: 5,944,970
[45] Date of Patent: Aug. 31, 1999

[54] SOLID STATE ELECTROCHEMICAL SENSORS

[75] Inventor: David Rosenblatt, Philadelphia, Pa.

[73] Assignee: Honeywell Inc., Minneapolis, Minn.

[21] Appl. No.: 08/841,031

[22] Filed: Apr. 29, 1997

[51] Int. Cl.⁶ .................................................. G01N 27/333
[52] U.S. Cl. .......................... 204/416; 204/418; 257/253; 438/142; 438/689
[58] Field of Search .................................. 204/416, 418, 204/419, 420; 257/253

[56] References Cited

U.S. PATENT DOCUMENTS

| | | | |
|---|---|---|---|
| 2,563,062 | 8/1951 | Perley | 204/420 |
| 4,020,830 | 5/1977 | Johnson et al. | 204/418 |
| 4,505,799 | 3/1985 | Baxter | 204/416 |
| 4,743,954 | 5/1988 | Brown | 357/25 |
| 4,961,833 | 10/1990 | Sakai et al. | 204/416 |
| 5,039,390 | 8/1991 | Hampp | 204/416 |
| 5,407,854 | 4/1995 | Baxter et al. | 437/54 |
| 5,414,284 | 5/1995 | Baxter et al. | 257/253 |

FOREIGN PATENT DOCUMENTS

| | | | |
|---|---|---|---|
| 0307973 | 3/1989 | European Pat. Off. . | |
| 43 33875 | 4/1995 | Germany . | |
| 667471 | 3/1952 | United Kingdom | 204/420 |
| WO87 03687 | 6/1987 | WIPO . | |
| WO 90 01694 | 2/1990 | WIPO . | |

OTHER PUBLICATIONS

Popova, L.I. "Conductive-oxide-gate FET as a gas sensor", *Sensor and Actuator B*, vol. B3, No. 4, Apr. 1, 1991, pp. 273–277.

Baxter et al, "Development and Performance Characteristics of A Nerw H Electrode", presented at the Pittsburg Conference 1992, New Orleans, LA, Mar. 10, 1992, (paper #561).

*Primary Examiner*—T. Tung
*Attorney, Agent, or Firm*—Joseph J. Kaliko; Anthony Miologos

[57] ABSTRACT

A solid state electrochemical sensor includes a conductive base layer which supports a chemically sensitive membrane, a guard ring layer located below the base layer and insulated therefrom by a dielectric insulator ring layer. The two ring layers define a central hole through which access to the underside of the base layer is provided. The side wall of the hole is coated with a dielectric oxide layer and a metal conductor is laid on the oxide layer and is ohmically bonded to the base layer. A second dielectric oxide layer covers the metal conductor and a metallic inner guard layer covers the second dielectric oxide layer and is in ohmic contact with the guard ring layer. A CMOS buffer amplifier (voltage follower amplifier) is formed on the lower surface of the guard ring layer. The input to the buffer amplifier is coupled to the conductor in ohmic contact with the base layer and the output of the buffer amplifier is coupled to the guard ring. The guard ring and the metallic inner guard layer form an active shield (guard) around the conductor which transmits the potential of the membrane to the amplifier. The amplifier powers the guard to the same potential as the membrane which insures that the membrane potential is read properly without corruption due to capacitive loading by parasitics, shorting caused by leakage currents, or capacitively coupled noise.

16 Claims, 11 Drawing Sheets

SOLID STATE ELECTROCHEMICAL SENSORS

BACKGROUND OF THE INVENTION

1. Field of the Invention

The invention relates to solid state electrochemical sensors. More particularly, the invention relates to electrochemical sensors which are submersed in a solution, such as pH sensors and the like.

2. State of the Art

In the late 1960s, Dutch researcher Piet Bergveld investigated the pH sensitivity of an electronic device known as an ion selective field effect transistor (ISFET). ISFETs are similar to conventional insulated gate FETs (field effect transistors) except that the metal gate electrode is removed and the gate region is covered with an insulator film. The film acts as an ion selective, sensitive membrane which affects the conductance between the drain and the source terminals of the transistor. Depending on the material chosen for the membrane, the membrane will react to different kinds of ionic activity. When the membrane is made of silicon nitride or aluminum oxide, it will react to hydrogen ions and the device can be used to measure pH.

In order for an ISFET to be useful in measuring the pH of a solution, it must be submersed in the solution. This raises many design problems since the solution is most often hostile to the ISFET circuit. It is therefore desirable to isolate the membrane from the other parts of the ISFET circuit so that the membrane may be in contact with the solution while the remainder of the ISFET circuit is protected from the adverse affects of the solution.

U.S. Pat. No. 4,505,799, the complete disclosure of which is hereby incorporated by reference herein, discloses an ISFET sensor and a method of manufacturing the sensor. The ISFET sensor 10, which is shown in prior art FIG. 1, includes an N-Si silicon crystal substrate 12 having an orientation of (100) which is coated on the top surface with a number of oxides 14 and an ion sensitive membrane 16. The substrate 12 is doped to have a P+ drain region 18 and a P+ source region 20. A window 21 is formed in the field oxide 13 in the area between the source and drain where the gate oxide 22 has been grown under the ion sensitive membrane 16. On the bottom surface of the substrate 12, windows 25, 27, and 29 are formed in the field oxide coating 15. Window 25 provides a substrate contact 24 to an N+ region 26. Windows 27 and 29 provide access to a source contact 28 and a drain contact 30. These contacts 28 and 30 are made through holes 31, 33 which are etched in the underside of the substrate. The sidewalls of the holes are provided with isolating P+ regions 35, 37 for isolating the substrate. The P+ regions 35, 37 are each coated with a metallization 39, 41 to provide electrical connections from the source contact 28 to the source 20 and from the drain contact 30 to the drain 18. The ISFET is then mounted in a probe body such that only a portion of the top surface of the substrate is exposed.

While the ISFET described in the '799 patent is an effective improvement over earlier ISFET devices, the method used to make it is relatively complex. A single transistor is formed on one side of the substrate and two etched holes must be provided on the other side to access the source and drain of the transistor. As with all transistors, the performance of the transistor will be subject to a number of different parameters including ambient temperature. Since pH is also affected by temperature, the reliability of the output of the ISFET will be temperature dependent.

SUMMARY OF THE INVENTION

It is therefore an object of the invention to provide an electrochemical sensor which is relatively easy to fabricate.

It is also an object of the invention to provide an electrochemical sensor which provides a reliable output throughout a wide range of temperatures.

It is another object of the invention to provide an electrochemical sensor which may be submersed in a hostile solution without suffering adverse effects.

It is still another object of the invention to provide a solid state electrochemical sensor for measuring pH.

It is yet another object of the invention to provide methods for making an electrochemical sensor satisfying the above stated objects.

In accord with these objects which will be discussed in detail below, the solid state electrochemical sensor of the present invention includes a polysilicon base layer which supports a chemically sensitive membrane, a degenerately doped P+ diffused guard ring layer located below the polysilicon layer and insulated therefrom by a dielectric insulator ring layer. The two ring layers define a central hole through which access to the underside of the polysilicon layer is provided. The side wall of the hole is coated with a dielectric oxide layer and a metal conductor is laid on the oxide layer and is ohmically bonded to the polysilicon layer. The conductor terminates on the lower surface of the guard ring layer. A second dielectric oxide layer covers the metal conductor and a metallic inner guard layer covers the second dielectric oxide layer and is in ohmic contact with the guard ring layer. A CMOS buffer amplifier (voltage follower amplifier) is formed on the lower surface of the guard ring layer. The input to the buffer amplifier is coupled to the conductor in ohmic contact with the base layer and the output of the buffer amplifier is coupled to the guard ring. The guard ring and the metallic inner guard layer form an active shield (guard) around the conductor which transmits the potential of the membrane to the amplifier. The amplifier powers the guard to the same potential as the membrane which insures that the membrane potential is read properly without corruption due to capacitive loading by parasitics, shorting caused by leakage currents, or capacitively coupled noise. In addition, as the amplifier is comprised of two transistors which are formed on the same wafer, the output of the amplifier is automatically corrected for variations in temperature. Furthermore, as all of the sensitive circuitry is located on the underside of the sensor, the circuitry is easily protected from contacting the solution in which the sensor may be submersed.

A first method of making the sensor includes depositing a small circular layer of SiN on the upper surface of a polysilicon guard layer, growing a thermal oxide over the upper surface of the guard layer and the SiN layer, etching back the thermal oxide to expose the SiN layer, depositing a base layer of P+ polysilicon on top of the thermal oxide and the SiN layer, etching an anisotropic pit in the underside of the guard layer to expose the underside of the SiN layer, subjecting the side wall of the pit to P+ diffusion, growing a thermal oxide layer over the P+ diffused side wall and the underside of the SiN layer, etching back the oxide layer to expose the underside of the SiN layer, removing the exposed portion of the SiN layer with acid, depositing an inner metal conductor over the oxide coating on the side wall and in ohmic contact with the base layer, depositing a dielectric coating over the inner conductor, depositing an inner guard conductor over the dielectric coating, depositing a membrane on the upper surface of the base layer, and depositing a protective coating around the periphery of the membrane and the base layer. In addition to these steps, a CMOS buffer amplifier is formed on the underside of the guard layer in a conventional manner and the inner metal conductor and the guard layer are electrically coupled to the buffer amplifier as described above.

A second method of making the sensor includes depositing a small circular layer of silicon dioxide on the upper surface of a polysilicon guard layer, stripping off the oxide and depositing a thin layer of SiN, depositing a base layer of P+ polysilicon on top of the SiN layer, etching an anisotropic pit in the underside of the guard layer to expose the underside of the SiN layer, subjecting the side wall of the pit to P+ diffusion, growing a wet oxide layer over the P+ diffused side wall and the underside of the SiN layer, etching back the oxide layer to expose the underside of the SiN layer, etching through the SiN layer to expose the underside of the base layer, depositing an inner metal conductor over the oxide coating on the side wall and in ohmic contact with the base layer, depositing a dielectric coating over the inner conductor, depositing an inner guard conductor over the dielectric coating, depositing a membrane on the upper surface of the base layer, and depositing a protective coating around the periphery of the membrane and the base layer. In addition to these steps, a CMOS buffer amplifier is formed on the underside of the guard layer in a conventional manner and the inner metal conductor and the guard layer are electrically coupled to the buffer amplifier as described above.

Presently preferred aspects of the first method of the invention include: performing the P+ diffusion of the guard ring pit side wall at greater than $7 \times 10^{20}$ cm$^{-3}$ to form a good conductor and an anisotropic etch stop, and using CVD processes to deposit the dielectric and conductive layers on the side wall. Presently preferred aspects of the second method of the invention include: making the SiN layer as thin as possible, and choosing an etch with low selectivity between nitride and oxide.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
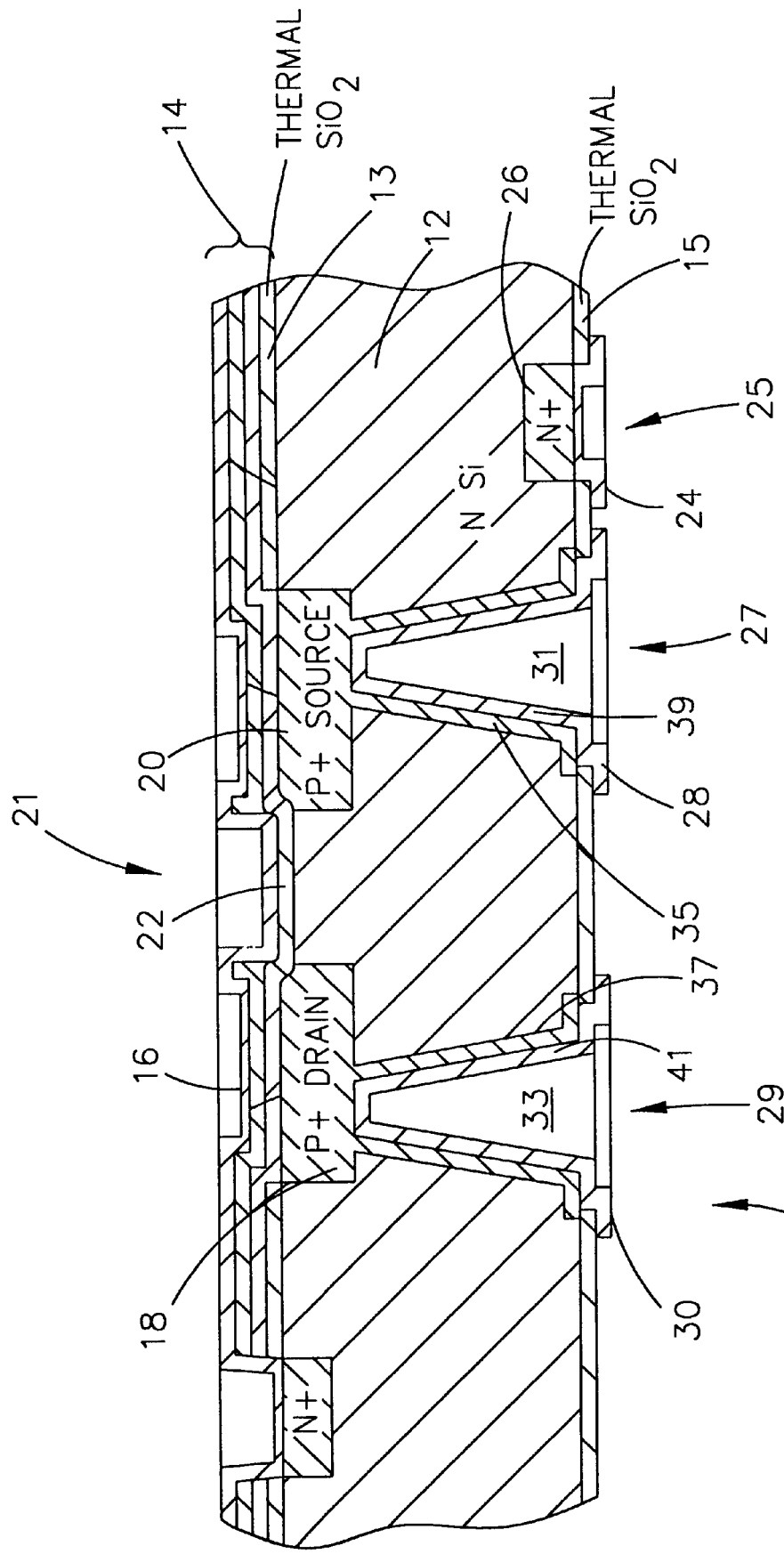
FIG. 1 is a cross section of an ISFET according to the prior art.
Figure 2:
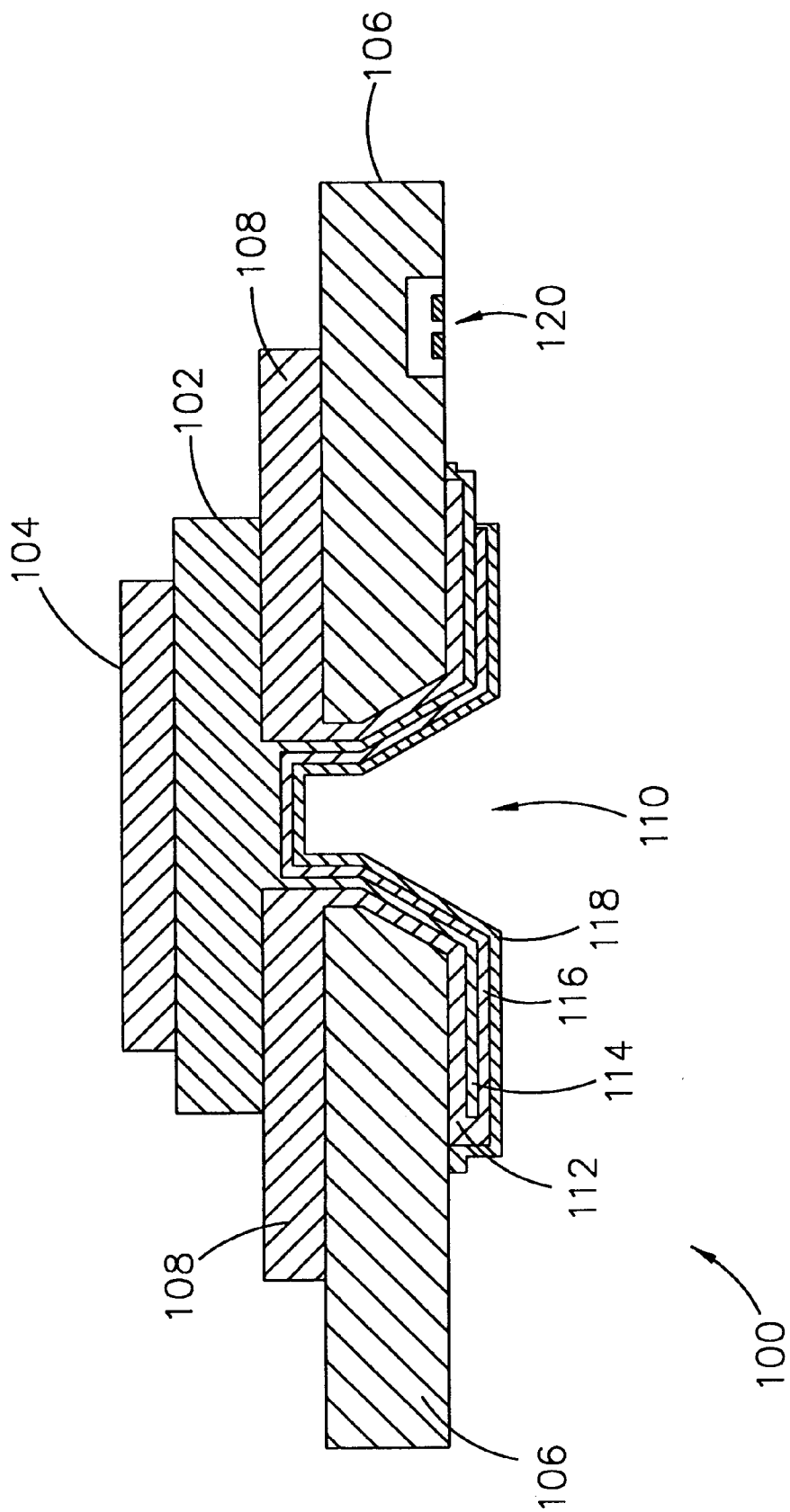
FIG. 2 is a schematic cross section of a solid state electrochemical sensor according to the invention.

Referring now to FIG. 2, a solid state electrochemical sensor 100 includes a polysilicon base layer 102 which supports a chemically sensitive membrane 104. A degenerately doped P+ diffused guard ring layer 106 is located below the polysilicon layer and insulated therefrom by a dielectric insulator ring layer 108. The two ring layers 106, 108 define a central hole 110 through which access to the underside of the polysilicon layer 102 is provided. The side wall of the hole 110 is coated with a first dielectric oxide layer 112, a first conductive layer 114, a second dielectric layer 116, and a second conductive layer 118. Each of the layers 112–118 continues onto the lower surface of the guard ring 106 forming a layered annular ring. The second conductive layer 118 is formed to electrically contact the guard ring 106 on the lower surface thereof. A CMOS buffer amplifier 120 is formed on a portion of the lower surface of the guard ring 106. The guard ring 106 and the first conductive layer 114 are electrically coupled to the amplifier 120 as described in more detail below.

Figure 3:
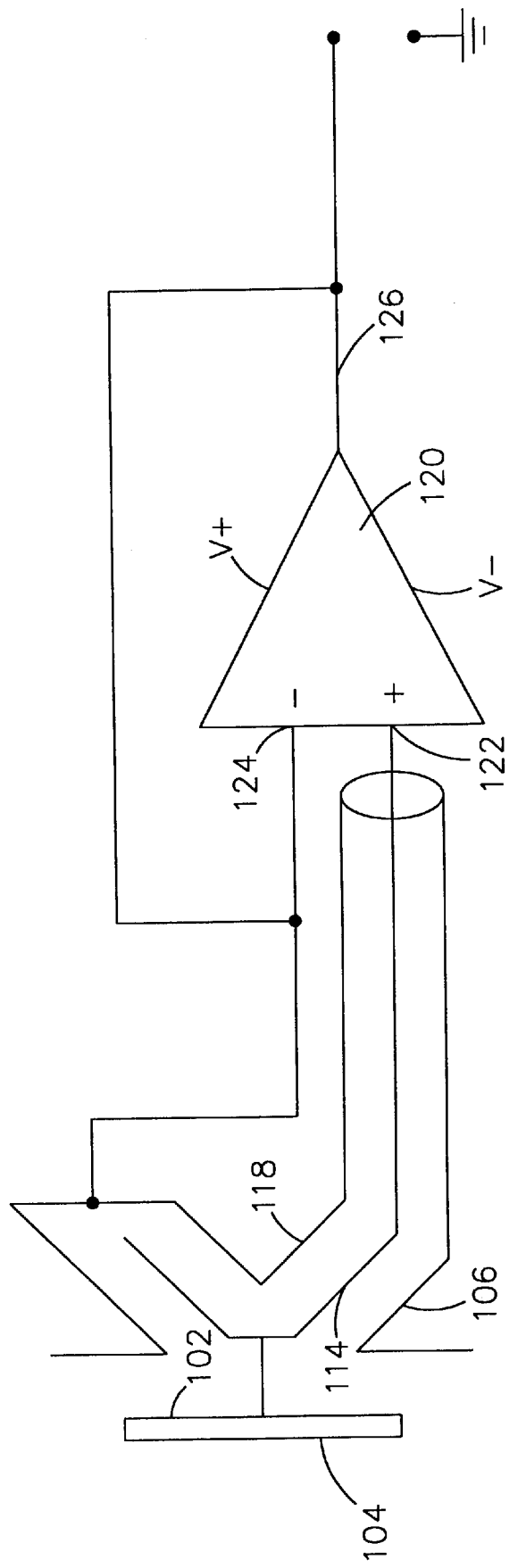
FIG. 3 is a simplified schematic diagram of the electrical circuit of the sensor according to the invention.

Referring now to FIG. 3, the amplifier 120 has a noninverting input 122, an inverting input 124, and an output 126. The output 126 of the amplifier 120 is fed back to the inverting input 124 to form a "buffer amplifier" or "voltage follower amplifier".

With reference now to FIGS. 2 and 3, the first conductive layer 114 is electrically coupled to the non-inverting input 122 of the amplifier 120, and the second conductive layer 118 is electrically coupled to the output 126 of the amplifier 120. From the foregoing, those skilled in the art will appreciate that the electrical potential of the membrane 104 is electrically conducted to the non-inverting input 122 of the amplifier 120 via the polysilicon layer 102 and the first conductive layer 114 and is faithfully reproduced at the output 126 of the amplifier 120. In addition, it will be appreciated that the guard ring 106 and the second conductive layer 118 form an electrical shield or guard surrounding the conductor 114. Moreover, the electrical coupling of the output 126 of the amplifier 120 to the conductive layer 118 makes the guard "active", powering it to the same potential as the membrane 104. This insures that the membrane potential is read properly without corruption due to capacitive loading by parasitics, shorting caused by leakage currents, or capacitively coupled noise. In addition, as the amplifier is comprised of two transistors which are formed on the same wafer, the output of the amplifier is automatically corrected for variations in temperature.

The above described device may be advantageously utilized as an electrochemical sensor, e.g. a pH sensor when used in conjunction with a reference electrode (not shown). When so utilized, the device 100 will be mounted in a probe body so that the membrane 104 is exposed, but the remainder of the device is shielded and protected from contact with fluid. The probe body and mounting procedures described in the above-referenced U.S. Pat. No. 4,505,799 or any other suitable mounting arrangement may be used. In use, the reference electrode or the amplifier will be biased relative to the other to create a potential on the surface of the membrane. Those skilled in the art of electrochemical sensing will appreciate that there are many different biasing schemes which could be used to provide the proper potential on the surface of the membrane.

The "actively guarded pass through" arrangement of the invention may be utilized in any type of solid state device which is used to faithfully reproduce a low level potential of a "sensor" on one side of the device to a circuit on the other side of the device. Although the primary applications for the invention are electrochemical sensors, the concepts of the invention could be applied to other types of sensors.

From the foregoing, those skilled in the art will appreciate that the device of the invention may be manufactured in several different ways applying known etching and deposition methods. The dimensions of the various components of the device will be matters of design choice which will bear on the durability of the device as well as the cost of manufacturing the device. Two possible, though not necessarily preferable, methods of making the device are described below.

Figure 4:
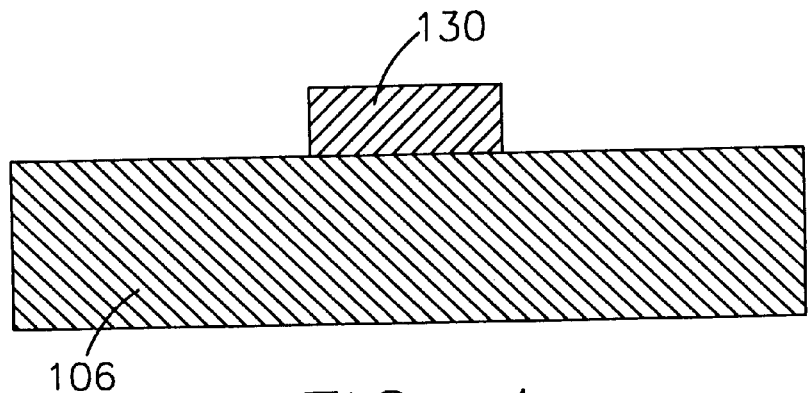
FIGS. 4–14 are schematic cross sections illustrating a first method of manufacture according to the invention.
Figure 5:
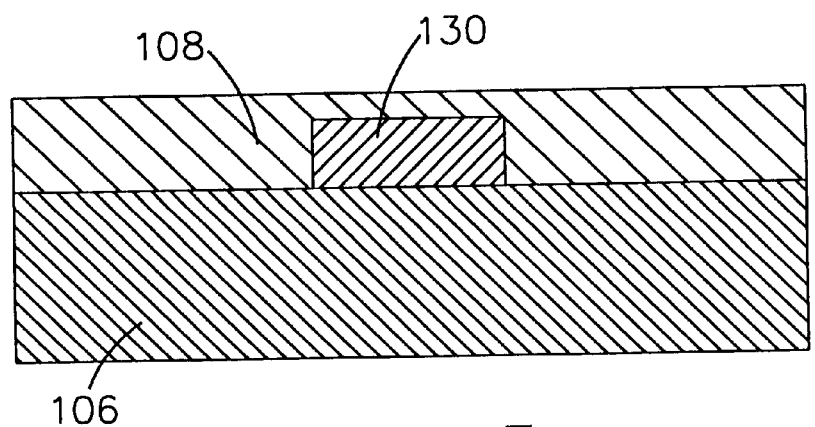

Referring now to FIGS. 4–14 (which are merely schematic and are not drawn to scale), a first method of making the sensor described above begins with the step (FIG. 4) of depositing and patterning a small circular layer of SiN 130 on the upper surface of layer 106. The nitride layer will be used later in the process as a mask for etching and P+ diffusion. Since diffusion under the nitride mask may define a lip around the circular layer of nitride, the aspect ratio of the layer 130 should be minimal.

Figure 6:
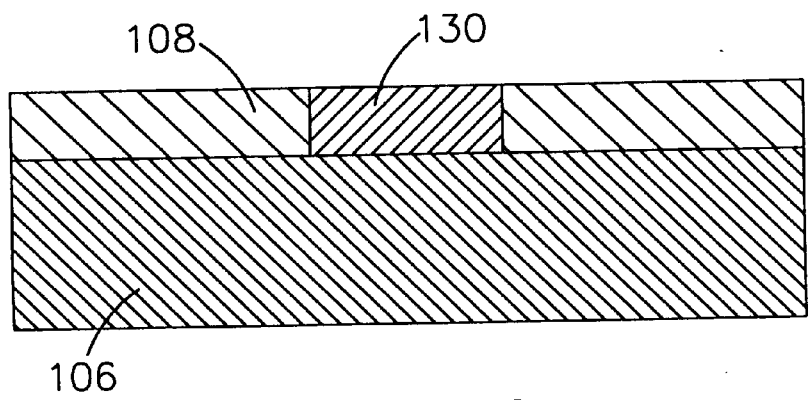
Figure 7:
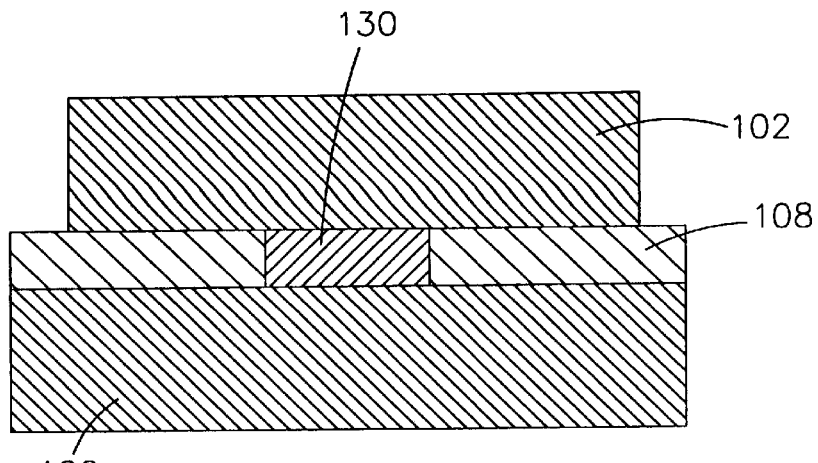
Figure 8:
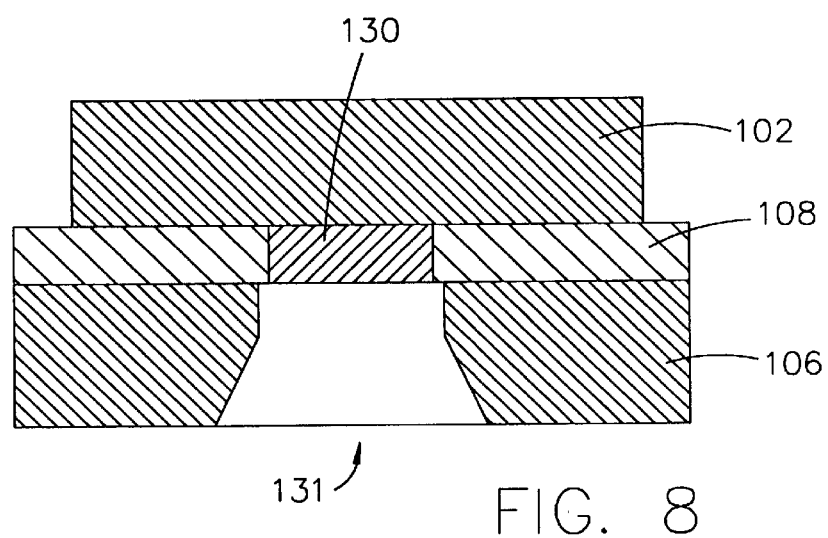
Figure 9:
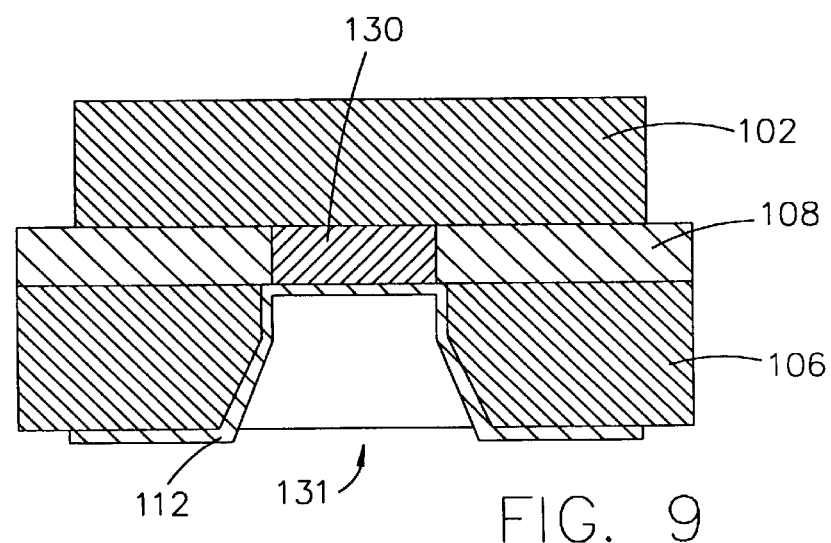

A thermal oxide 108 (FIG. 5) is then grown over the upper surface of layer 106 and the SiN layer 130. The oxide layer 108 is then etched back to expose the nitride layer 130 as shown in FIG. 6.

A layer of P+ polysilicon 102 (FIG. 7) is then deposited on top of the oxide layer 108 and the nitride layer 130. The polysilicon layer 102 will be used as the supporting base for the membrane and should be thick enough to be mechanically robust.

A pit 131 (FIG. 8) is then anisotropically etched in layer 106 from its bottom or back surface to expose the underside of the nitride layer 130. If the layer 106 is sufficiently thick, over etching will not compromise the mechanical integrity of the layer, but may result in a lip (obstruction of continuity) which will cause bends in the conductive and non-conductive layers which will be later deposited in the pit. Over etching should therefore be avoided.

The side walls of the pit 131 are then subjected to P+ diffusion (not shown) to define the conductive portion of the guard ring. The diffusion step is preferably a deep diffusion ($>7 \times 10^{20}$ cm$^{-3}$)

Figure 10:
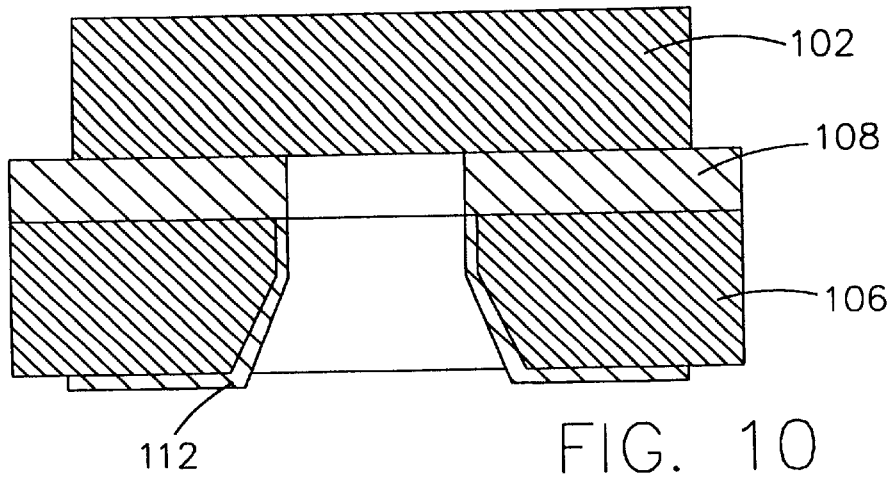
Figure 11:
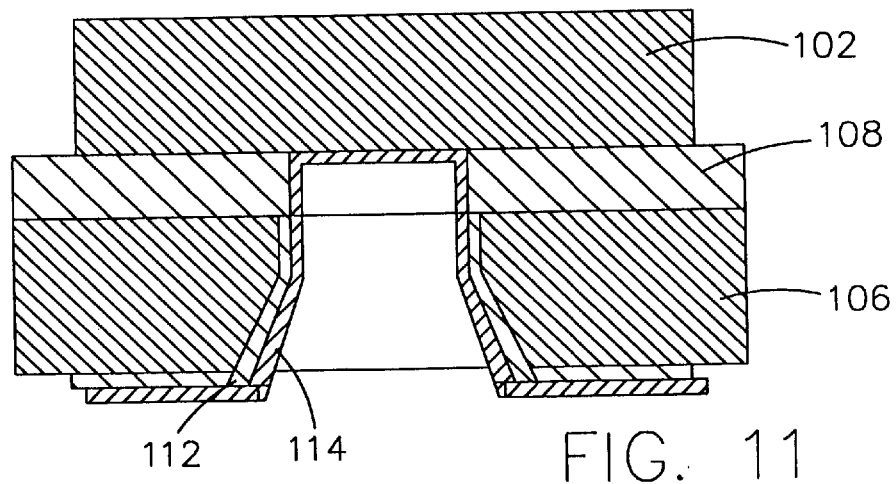
Figure 12:
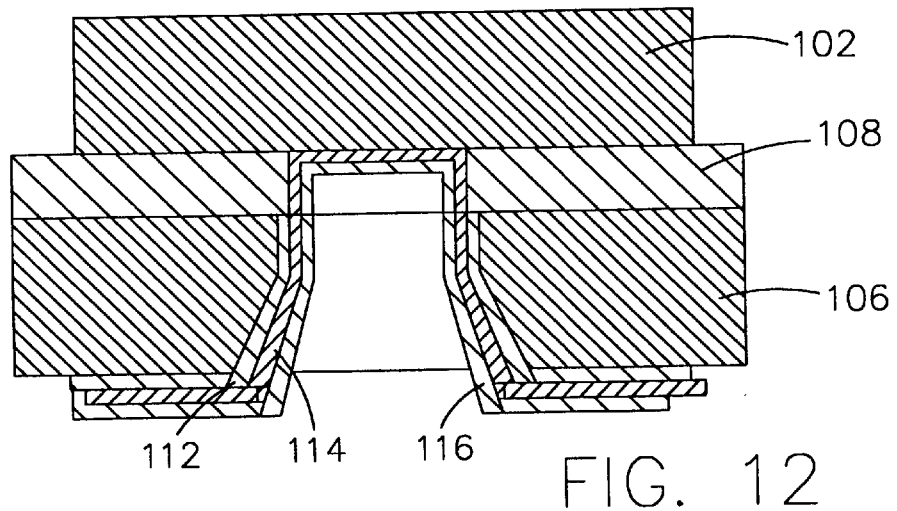
Figure 13:
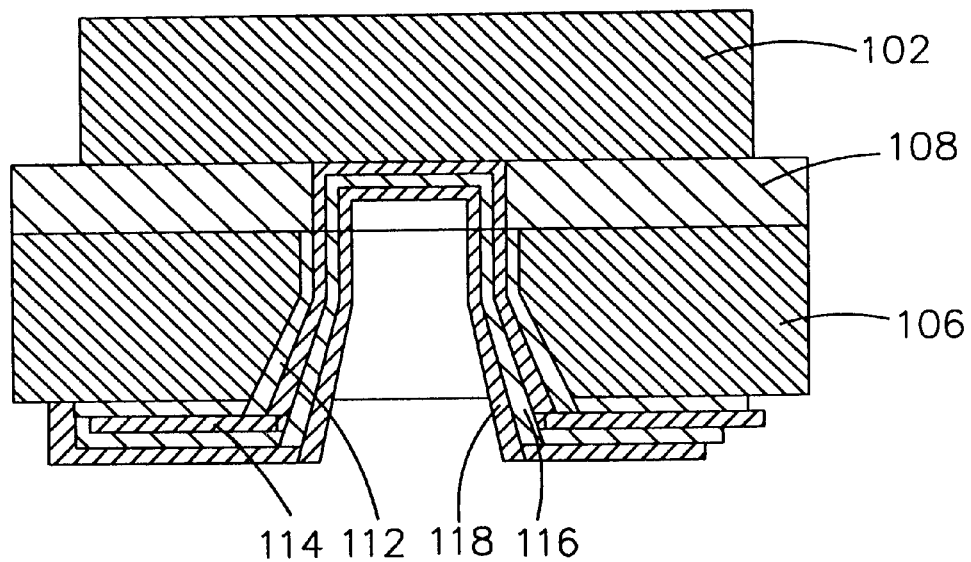
Figure 14:
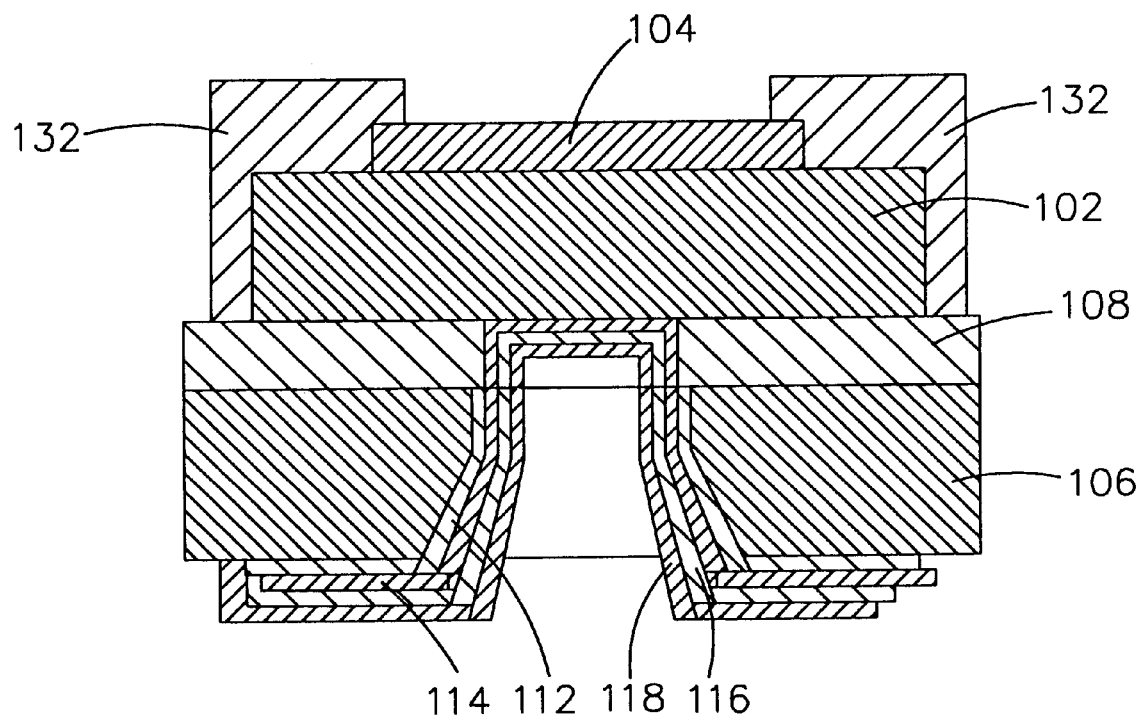
Figure 15:
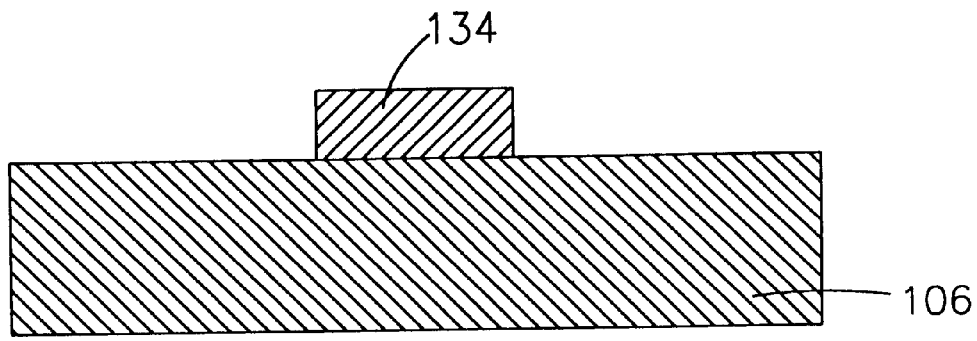
FIGS. 15–25 are schematic cross sections illustrating a second method of manufacture according to the invention.
Figure 16:
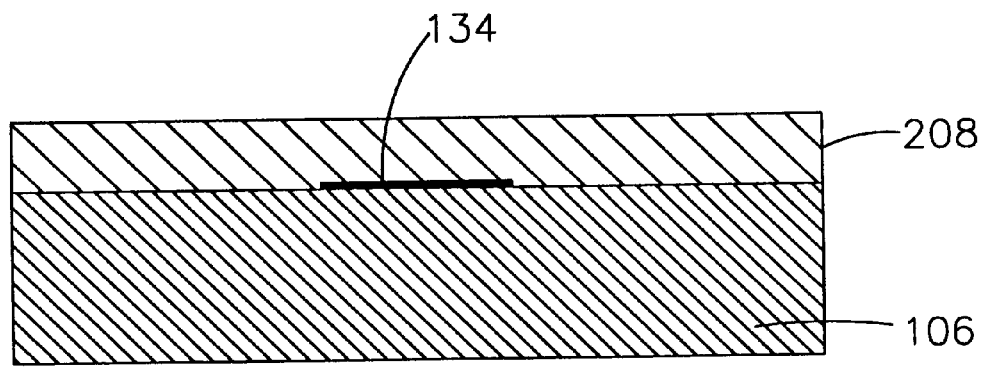
Figure 17:
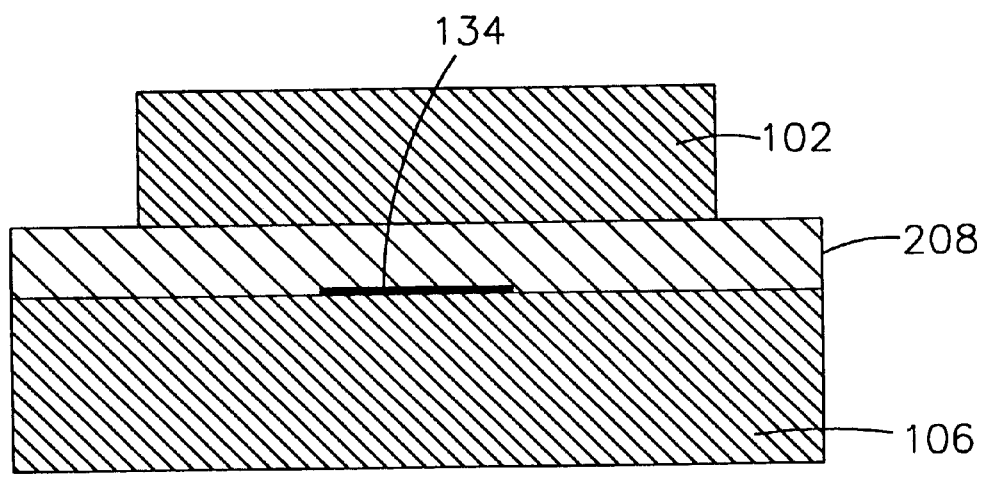
Figure 18:
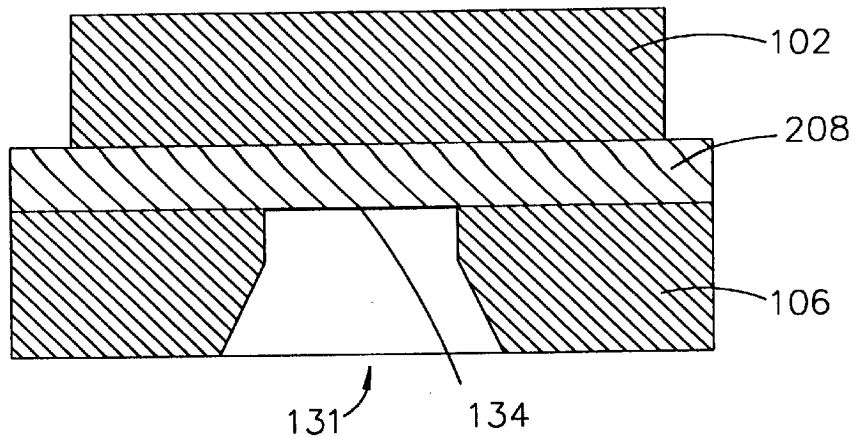
Figure 19:
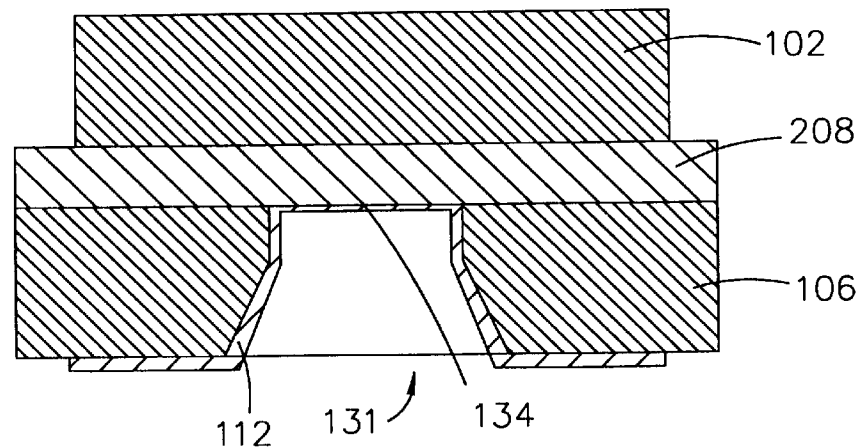

A thermal oxide layer 112 (FIG. 9) is then grown on the inside surface of the pit 131 as well as on the underside of the nitride layer 130. The layer my be advantageously applied using a CVD process. This layer 112 will serve as a dielectric insulator between the guard ring and the potential conductor. The portion of the oxide layer 112 lying on the nitride layer 130 is then etched back and the nitride layer is removed with hot phosphoric acid to reveal the underside of the polysilicon layer 102 as shown in FIG. 10.

A conductive layer 114 (FIG. 11) is then applied (by CVD) to the interior of the pit. This layer will form an electrical connection with the polysilicon layer 102 and provide a conductive path to the underside of the layer 106. The conductive layer 114 is insulated from the conductive portion of the guard ring by the dielectric layer 112.

A second dielectric layer 116 (FIG. 12) is then applied on top of the conductive layer 114 and a second conductive layer 118 (FIG. 13) is applied on top of the dielectric layer 116. The second conductive layer 118 is electrically coupled (by the deposition process) to the guard ring layer 106 thereby completing a conductive shield around the potential conductor 114.

An electrochemically sensitive membrane 104 (FIG. 14) is then deposited on the top surface of the polysilicon layer 102 and a protective coating 132 is added around the edges of the membrane and the membrane supporting base 102.

The final step in making the sensor is not illustrated, but is performed in a conventional manner using known masking and deposition techniques. The final step includes forming an amplifier on the bottom surface of the guard ring 106 and coupling the conductors to the amplifier as described above.

Referring now to FIGS. 15–25, a second method of making the sensor avoids the formation of a lip at the base of the pit by using a single layer of silicon nitride as the dielectric insulator between the membrane supporting layer and the guard ring layer. The first step in this method is to grow and pattern a silicon dioxide mask 134 (FIG. 15) on the upper surface of layer 106. This mask is then all but removed and a thin layer of silicon nitride 208 (FIG. 16) is deposited on the surface of layer 106.

A relatively thick base layer of P+ polysilicon 102 (FIG. 17) is deposited on top of the SiN layer, and an. anisotropic pit 131 (FIG. 18) is etched in the underside of the layer 106 to expose the oxide 134 coated underside of the SiN layer 208.

Figure 20:
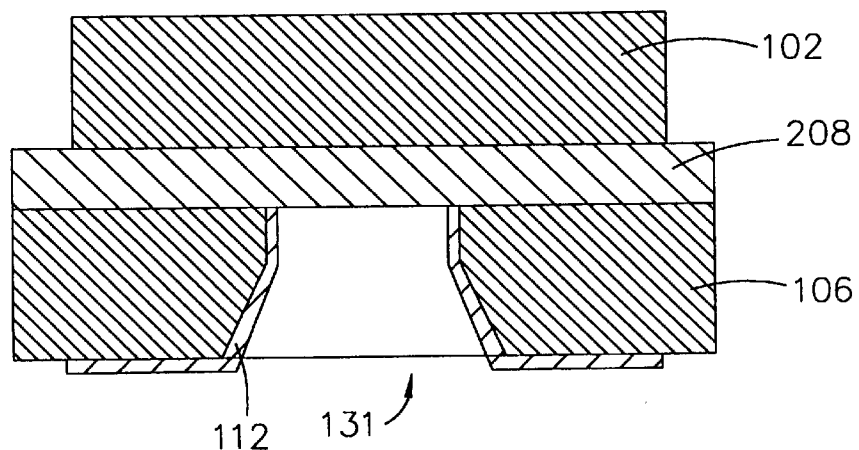
Figure 21:
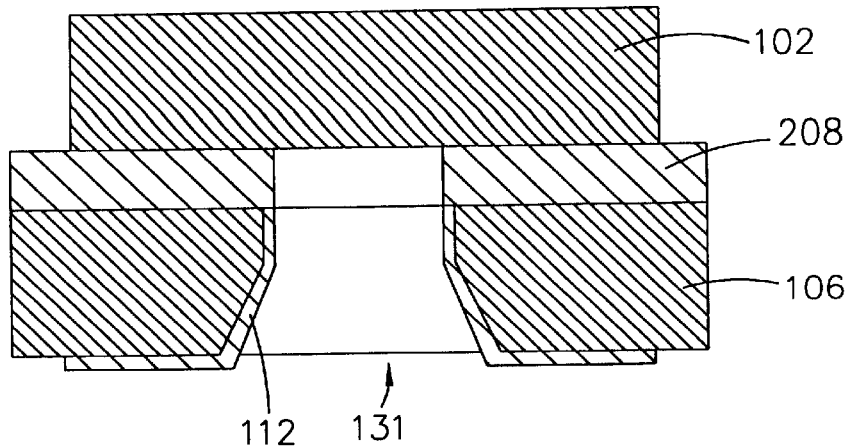
Figure 22:
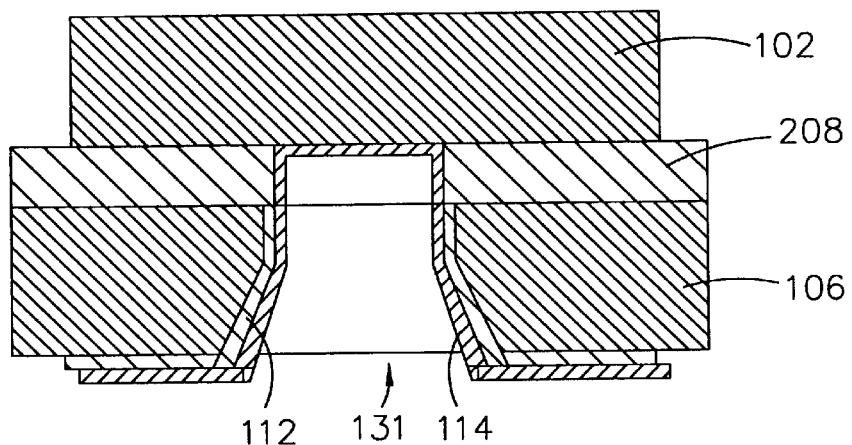
Figure 23:
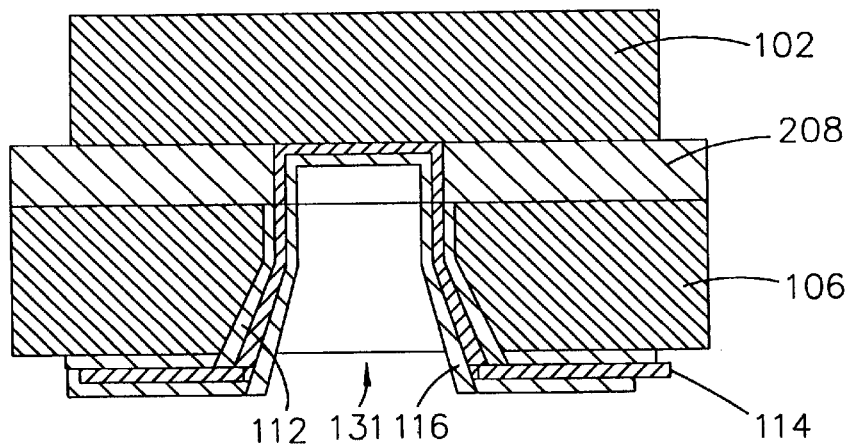
Figure 24:
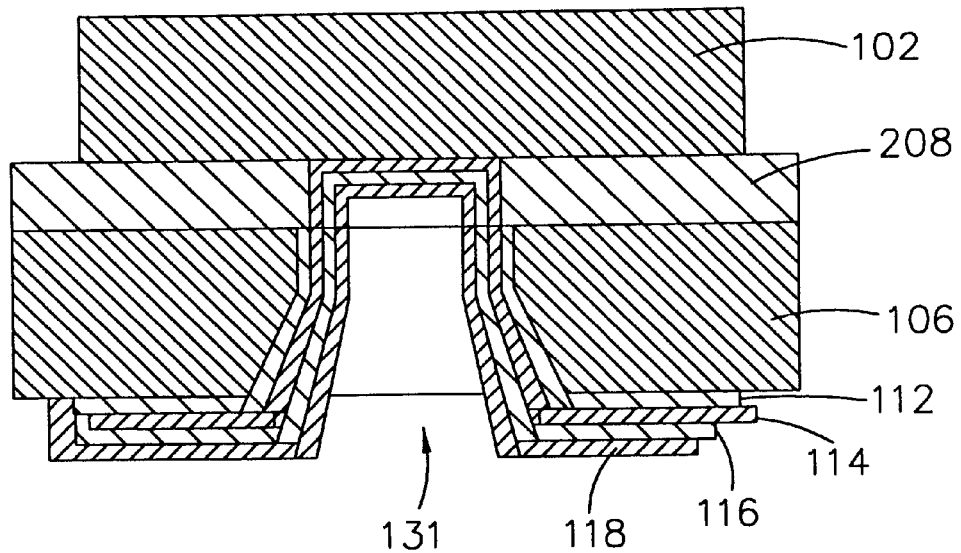
Figure 25:
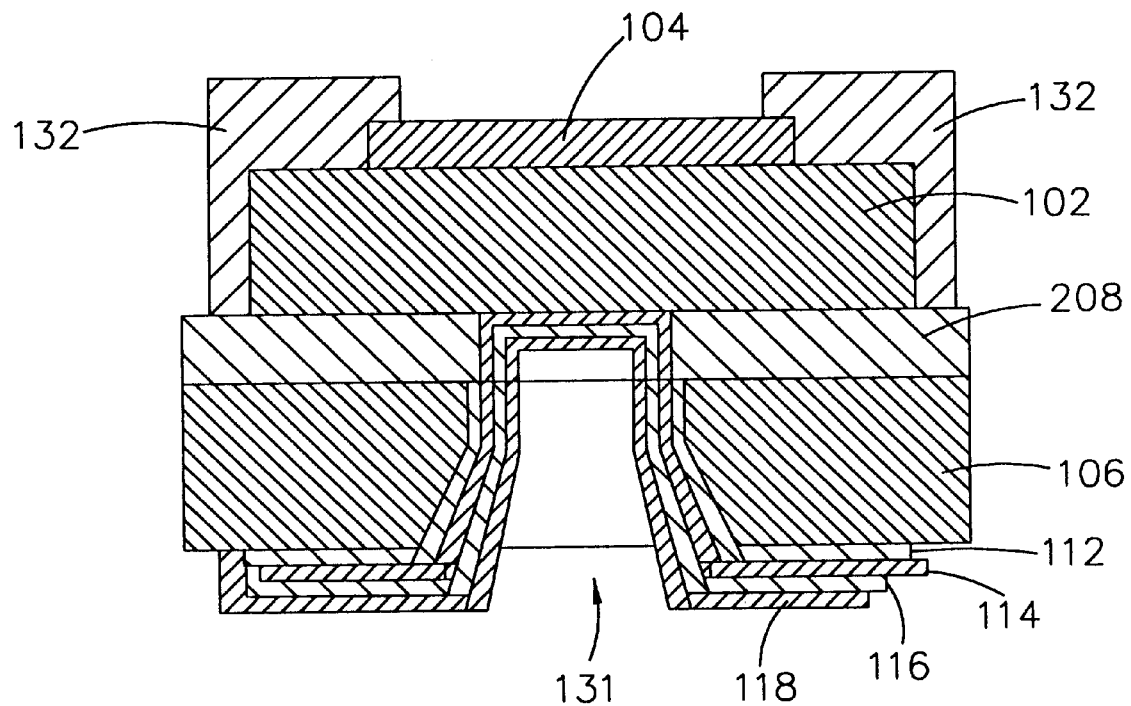

The side wall of the pit 131 is subjected to P+ diffusion (not shown) and a wet oxide layer 112 (FIG. 19) is grown over the P+ diffused side wall and the oxide coated underside of the SiN layer. The oxide layer 112 is then etched back to expose the underside of the SiN layer 208 (FIG. 20). The etching step is preferably performed with an etching process which has low selectivity between nitride and oxide to avoid formation of a lip by undercutting.

The exposed portion of the SiN layer 208 is then etched through to the polysilicon layer 102 (FIG. 21) and an inner metal conductor 114 (FIG. 22) is deposited, sintered or alloyed over the oxide coating on the side wall and in ohmic contact with the base layer 208.

A dielectric coating 116 (FIG. 23) is deposited over the conductor 114, and an inner guard conductor 118 (FIG. 24) is deposited over the dielectric coating 116. The membrane 104 (FIG. 25) is then deposited on the upper surface of the base layer 102, and a protective coating 132 is deposited around the periphery of the membrane and the base layer. In addition to these steps, a CMOS buffer amplifier is formed on the underside of the guard layer in a conventional manner and the inner metal conductor and the guard layer are electrically coupled to the buffer amplifier as described above.

Presently preferred aspects of the first method of the invention include: performing the P+ diffusion of the guard ring pit side wall at greater than $7 \times 10^{20}$ cm$^{-3}$ to form a good conductor and an anisotropic etch stop, and using CVD processes to deposit the dielectric and conductive layers on the side wall. Presently preferred aspects of the second method of the invention include: making the SiN layer as thin as possible, and choosing an etch with low selectivity between nitride and oxide.

There have been described and illustrated herein several embodiments of an electrochemical sensor and methods of making the sensor. While particular embodiments of the invention have been described, it is not intended that the invention be limited thereto, as it is intended that the invention be as broad in scope as the art will allow and that the specification be read likewise. Thus, while particular conductive and non-conductive materials have been disclosed, it will be appreciated that other materials could be utilized depending on the application of the device. Also, while particular geometries have been shown, it will be recognized that other geometries could be used with similar results obtained and that the crystalline structure of silicon will determine certain aspects of the geometry of the device.

Moreover, while particular configurations have been disclosed in reference to a protective coating around the edges of the membrane and the base member, it will be appreciated that other configurations could be used as well. Furthermore, while the device has been disclosed as having a certain number of layers, it will be understood that additional layers can achieve the same or similar function as disclosed herein. It will therefore be appreciated by those skilled in the art that yet other modifications could be made to the provided invention without deviating from its spirit and scope as so claimed.

What is claimed is:

1. A solid state sensor device, comprising:
   a) an ion-sensitive membrane mounted on an upper surface of said device;
   b) a first electrically conductive layer electrically coupled to said membrane and extending through said device to a lower surface of said device;
   c) a second electrically conductive layer substantially surrounding said first electrically conductive layer and being electrically insulated therefrom;
   d) a third electrically conductive layer electrically coupled to said second electrically conductive layer and electrically insulated from said first electrically conductive layer with said first electrically conductive layer lying between said second electrically conductive layer and said third electrically conductive layer, wherein
   said second electrically conductive layer and said third electrically conductive layer form a conductive shield around said first electrically conductive layer.

2. A solid state device according to claim 1, further comprising:
   e) a voltage-follower amplifier formed on said lower surface of said device, said amplifier having an input and an output, said input being electrically coupled to said first electrically conductive layer and said output being electrically coupled to said second and third electrically conductive layers.

3. A solid state device according to claim 1, wherein:
   each of said first, second and third electrically conductive layers exhibit a portion which is skewed relative to said upper and lower surfaces.

4. A solid state device according to claim 3, wherein:
   each of said first, second and third electrically conductive layers exhibit a substantially circular cross section.

5. A solid state device according to claim 1, further comprising:
   e) an upper conductive base member defining said upper surface; and
   f) a lower ring member defining said lower surface and defining a central throughbore having a side wall, wherein
   said first, second and third electrically conductive layers are formed in part as layers on said side wall.

6. A solid state device according to claim 5, further comprising:

g) a dielectric ring member interposed between said upper conductive base member and said lower ring member.

7. A solid state device according to claim 6, wherein:
   said upper conductive member is P+ polysilicon.

8. A solid state device according to claim 7, wherein:
   said lower ring member is degenerately doped P+.

9. A solid state device according to claim 8, wherein:
   said dielectric ring member is a thermal oxide.

10. A solid state device according to claim 8, wherein:
    said dielectric ring member is silicon dioxide.

11. A solid state electrochemical sensor, comprising:
    a) a conductive base layer having an upper surface and a lower surface;
    b) a chemically sensitive membrane mounted on said upper surface of said base layer;
    c) a dielectric ring layer having an upper surface and a lower surface, said upper surface of said dielectric ring layer contacting said lower surface of said base layer;
    d) a guard ring layer having an upper surface and a lower surface, said upper surface of said guard ring layer contacting said lower surface of said dielectric ring layer, said guard ring layer and said dielectric ring layer defining a central hole having a side wall which terminates at the lower surface of said base layer, said guard ring layer having an electrically conductive portion on said side wall;
    e) a first dielectric oxide layer coating said side wall;
    f) a first conductive layer coating said first dielectric oxide layer and being electrically coupled to said base layer;
    g) a second dielectric oxide layer coating said first conductive layer; and
    h) a second conductive layer coating said second dielectric oxide layer and being electrically coupled to said electrically conductive portion of said guard ring layer.

12. A sensor according to claim 11, further comprising:
    i) a voltage-follower amplifier formed on said lower surface of said guard ring layer, said amplifier having an input and an output, said input being electrically coupled to said first conductive layer and said output being electrically coupled to said second conductive layer.

13. A sensor according to claim 11, wherein:
    said conductive base layer is P+ polysilicon.

14. A sensor according to claim 13, wherein:
    said guard ring layer is degenerately doped P+.

15. A sensor according to claim 14, wherein:
    said dielectric ring layer is a thermal oxide.

16. A sensor according to claim 14, wherein:
    said dielectric ring layer is silicon dioxide.

* * * * *